US006287766B1

(12) United States Patent
Nolan et al.

(10) Patent No.: US 6,287,766 B1
(45) Date of Patent: *Sep. 11, 2001

(54) DNA POLYMORPHISM IDENTITY DETERMINATION USING FLOW CYTOMETRY

(75) Inventors: John P. Nolan, Santa Fe; P. Scott White; Hong Cai, both of Los Alamos, all of NM (US)

(73) Assignee: The Regents of the University of California, Los Alamos, NM (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/182,869

(22) Filed: Oct. 28, 1998

Related U.S. Application Data
(60) Provisional application No. 60/063,685, filed on Oct. 28, 1997.

(51) Int. Cl.[7] .............. C12Q 1/68; C12P 15/00; C07H 21/02; C07H 21/04; C12N 15/00
(52) U.S. Cl. .............. 435/6; 435/91.2; 536/23.1; 536/24.3; 935/76; 935/77; 935/78
(58) Field of Search .............. 35/6, 76, 77, 78, 35/91.2; 36/23.1, 24.3

(56) References Cited

U.S. PATENT DOCUMENTS 4,988,617 * 1/1991 Landegren et al. ............. 435/6

FOREIGN PATENT DOCUMENTS

WO9606950 * 3/1996 (WO).
WO9967414 12/1999 (WO) .............. C12P/1/68

OTHER PUBLICATIONS

Shumaker et al., Human Mutation 7 : 346–354 (1996).*
Ugozzoli et al., GATA 9(4) : 107–112 (1992).*
Vlieger et al., Analytical Biochemistry 205 : 1–7 (1992).*
T. Pastinen et al., "Minisequencing: A Specific Tool for DNA Analysis and Diagnostics on Oligonucleotide Arrays," Genome Research 7,606 (1997).
V. O. Tobe et al., "Single–Well Genotyping of Diallelic Sequence Variation by a Two–Color ELISA–Based Oligonucleotide Ligation Assay," Nuclear Acids Res. 24,3728 (1996).

* cited by examiner

Primary Examiner—Ethan Whisenant
(74) Attorney, Agent, or Firm—Samuel M. Freund

(57) ABSTRACT

DNA polymorphism identity determination using flow cytometry. Primers designed to be immobilized on microspheres are allowed to anneal to the DNA strand under investigation, and are extended by either DNA polymerase using fluorescent dideoxynucleotides or ligated by DNA ligase to fluorescent reporter oligonucleotides. The fluorescence of either the dideoxynucleotide or the reporter oligonucleotide attached to the immobilized primer is measured by flow cytometry, thereby identifying the nucleotide polymorphism on the DNA strand.

21 Claims, 5 Drawing Sheets

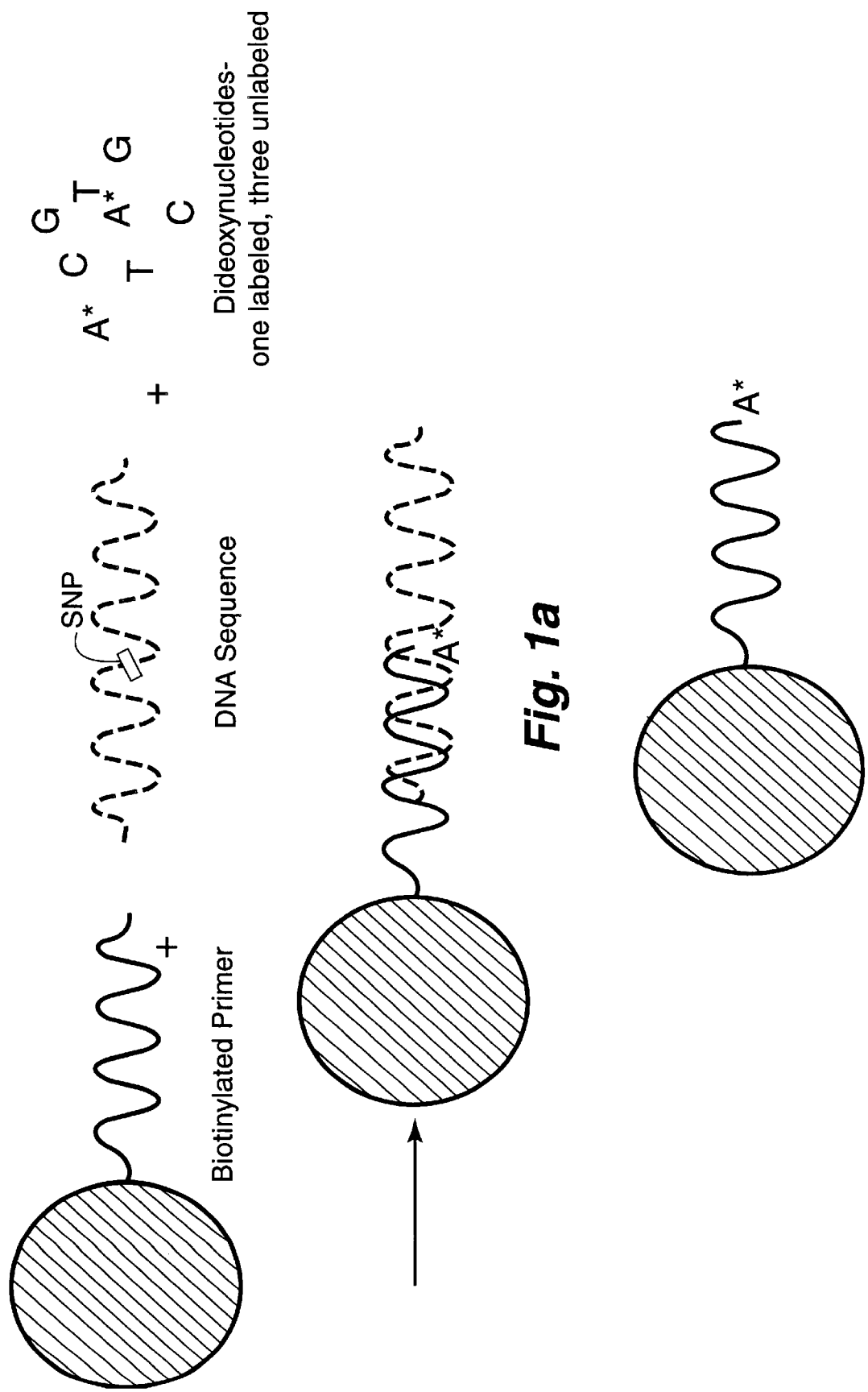

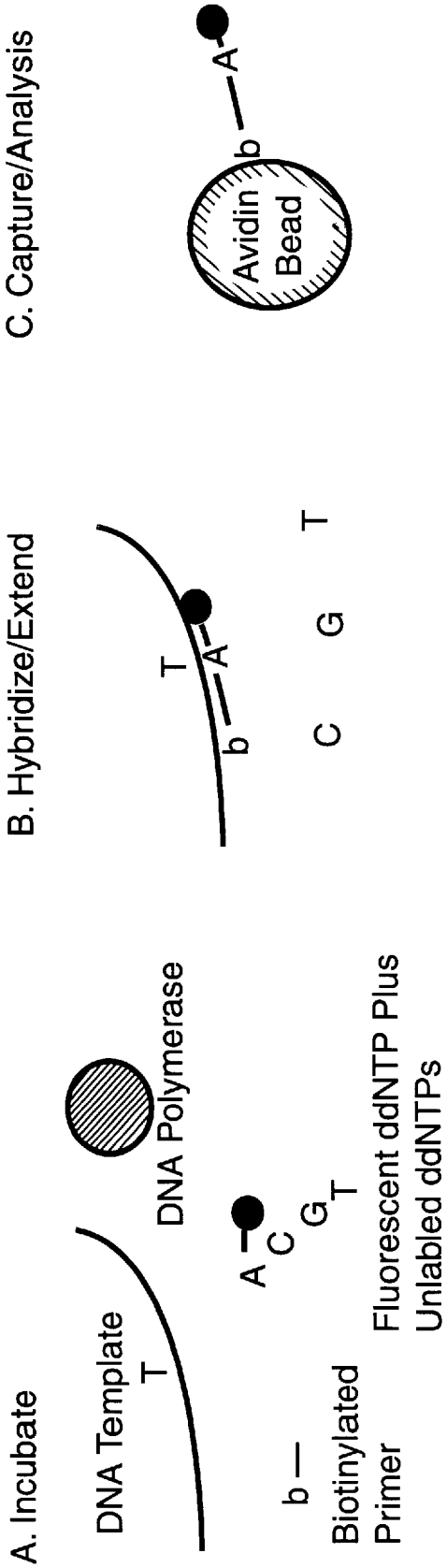

DNA POLYMORPHISM IDENTITY DETERMINATION USING FLOW CYTOMETRY

The present patent application claims priority from Provisional Patent Application No. 60/063,685, which was filed on Oct. 28, 1997.

The present invention relates generally to the use of flow cytometry for the determination of DNA nucleotide base composition and, more particularly, to the use flow cytometry to determine the base identification of single nucleotide polymorphisms, including nucleotide polymorphisms, insertions, and deletions. This invention was made with government support under Contract No. W-7405-ENG-36 awarded by the US Department of Energy to The Regents of The University of California. The government has certain rights in this invention.

FIELD OF THE INVENTION

BACKGROUND OF THE INVENTION

The determination of the DNA base sequence of the human genome will have a major impact on biomedical science in the next century. The completion of the first complete human DNA will enhance a range of applications from genetic mapping of disease-associated genes to diagnostic tests for disease susceptibility and drug response. The determination of base composition at specific, variable DNA sites known as single nucleotide polymorphisms (SNPs) is especially important. The current generation of sequence determination methods are too slow and costly to meet large-scale SNP analysis requirements. Thus, there is a need for faster, more efficient methods for analyzing genetic sequences for SNPs.

SNPs have a number of uses in mapping, disease gene identification, and diagnostic assays. All of these applications involve the determination of basEs composition at the SNP site. Conventional sequencing can provide this information, but is impractical for screening a large number of sites in a large number of individuals. Several alternative methods have been developed to increase throughput.

Two techniques have been developed to determine base composition at a single site, minisequencing (See, e.g., "Minisequencing: A Specific Tool For DNA Analysis And Diagnostics On Oligonucleotide Arrays," by Tomi Pastinen et al., Genome Research 7, 606 (1997)), and oligo-ligation (See, e.g., "Single-Well Genotyping Of Diallelic Sequence Variations By A Two-Color ELISA-Based Oligonucleotide Ligation Assay," by Vincent O. Tobe et al., Nuclear Acids Res. 24, 3728 (1996)). In minisequencing, a primer is designed to interrogate a specific site on a sample template, and polymerase is used to extend the primer with a labeled dideoxynucleotide. In oligo-ligation, a similar primer is designed, and ligase is used to covalently attach a downstream oligo that is variable at the site of interest. In each case, the preference of an enzyme for correctly base-paired substrates is used to discriminate the base identity that is revealed by the covalent attachment of a label to the primer. In most applications these assays are configured with the primer immobilized on a solid substrate, including microplates, magnetic beads and recently, oligonucleotides microarrayed on microscope slides. Detection strategies include direct labeling with fluorescence detection or indirect labeling using biotin and a labeled streptavidin with fluorescent, chemiluminescent, or absorbance detection.

Oligonucleotide microarrays or "DNA chips" have generated much attention for their potential for massively parallel analysis. The prospect of sequencing tens of thousands of bases of a small sample in just a few minutes is exciting. At present, this technology has limited availability in that arrays to sequence only a handful of genes are currently available, with substantial hardware and consumable costs. In addition, the general approach of sequencing by hybridization is not particularly robust, with the requirement of significant sequence-dependent optimization of hybridization conditions. Nonetheless, the parallelism of an "array" technology is very powerful. and multiplexed sequence determination is an important element of the new flow cytometry method.

Accordingly, it is an object of the present invention to provide a method for determining the base composition at specific sites in a strand of DNA using microspheres and flow cytometry, wherein the specificity of enzymes for discriminating base composition is combined with the parallel analysis of a fluorescent microsphere array.

Additional objects, advantages, and novel features of the invention will be set forth in part in the description which follows, and in part will become apparent to those skilled in the art upon examinations of the following or may be learned by practice of the invention. The objects and advantages of the invention may be realized and attained by means of the instrumentalities and combinations particularly pointed out in the appended claims.

SUMMARY OF THE INVENTION

To achieve the forgoing and other objects, and in accordance with the purposes of the present invention as embodied and broadly described herein, the method for determining the base composition at specific sites on a DNA strand hereof includes the steps of: preparing an oligonucleotide primer bearing an immobilization or capture tag, fluorescently labeled dideoxynucleotides; extending the oligonucleotide primer using DNA polymerase with the fluorescent dideoxynucleotide; specifically binding the tagged primers to microspheres; and measuring microsphere fluorescence by flow cytometry.

Preferably, the oligonucleotide primers are designed to anneal to the DNA sample under investigation immediately adjacent to the site of interest so as to interrogate the next nucleotide base on the DNA sample.

It is also preferred that the primers have on their 5' terminus one of: (a) an amino or other functional group suitable for covalent coupling to a microsphere; (b) a biotin group suitable for binding to avidin or streptavidin immobilized on a microsphere; or (c) an oligonucleotide tag that is complementary to an oligonucleotide capture probe immobilized on a microsphere surface.

In another aspect of the present invention, in accordance with its objects and purposes, the method for determining the base composition at specific sites on a DNA strand hereof includes the steps of: preparing an oligonucleotide primer bearing an immobilization or capture tag, fluorescently labeled dideoxynucleotides; preparing a fluorescent reporter oligonucleotide; enzymatically ligating the oligonucleotide primer to the fluorescent reporter oligonucleotide; specifically binding the tagged primers to microspheres; and measuring microsphere fluorescence by flow cytometry.

Benefits and advantages of the present invention include a sensitive, homogenous, and flexible method for determining DNA base composition at specific sites.

BRIEF DESCRIPTION OF THE DRAWINGS

The accompanying drawings, which are incorporated in and form part of the specification, illustrate an embodiment of the present invention and, together with the description, serve to explain the principles of the invention. In the drawings:

FIG. 1a is a schematic representation of microsphere-based minisequencing for flow cytometry, where a primer immobilized on a microsphere is used for hybridizing with the DNA sequence under investigation in the presence of dideoxynucleotides, at least one of which is fluorescently labeled, and polymerase, whereby the primer is extended by one base, while FIG. 1b is a schematic representation of the resulting primer having a single, fluorescent dideoxynucleotide bound to the end thereof which can be detected using flow cytometry, and represents the complementary base to the SNP on the DNA.

FIG. 2a is a schematic representation of microsphere-based minisequencing for flow cytometry similar to that described in FIGS. 1a and 1b hereof, except that soluble biotinylated primers and avidin-coated capture microspheres are used instead of primers which have already been immobilized on the microspheres, FIG. 2b shows the hybridization of the biotinylated primer to the DNA strand to be investigated and the extension of this primer by a fluorescent A dideoxynucleotide (assuming that the SNP is a T base) as a result of the DNA polymerase present in the solution, and FIG. 2c shows the capture of the extended biotinylated primer onto an avidin-coated microsphere after the hybridized DNA strand is melted, with the subsequent fluorescence analysis using flow cytometry.

FIG. 3a is a schematic representation of a multiplexed microsphere-based minisequencing procedure using soluble sequence-tagged primers and capture probe-bearing microspheres in a similar manner to the minisequencing illustrated in FIGS. 2a and 2b hereof, except that four SNPs have been assumed to be present on the DNA, strand, while FIG. 3b illustrates the microspheres and the captured extended primers to be analyzed using flow cytometry.

FIG. 4a is a schematic representation of microsphere-based oligonucleotide ligation assay using flow cytometry, where a primer immobilized on a microsphere along with fluorescent complementary primers for ligating to the primer which has hybridized to the DNA strand to be investigated in the region of the SNP, while FIG. 4b is a schematic representation of the microsphere-attached primer to which the proper fluorescent complement has been ligated after the DNA has been melted away, the flow cytometric determined fluorescence of the microsphere indicating which fluorescent complement has been attached to the DNA strand.

DETAILED DESCRIPTION

Figures 3A, 3B:
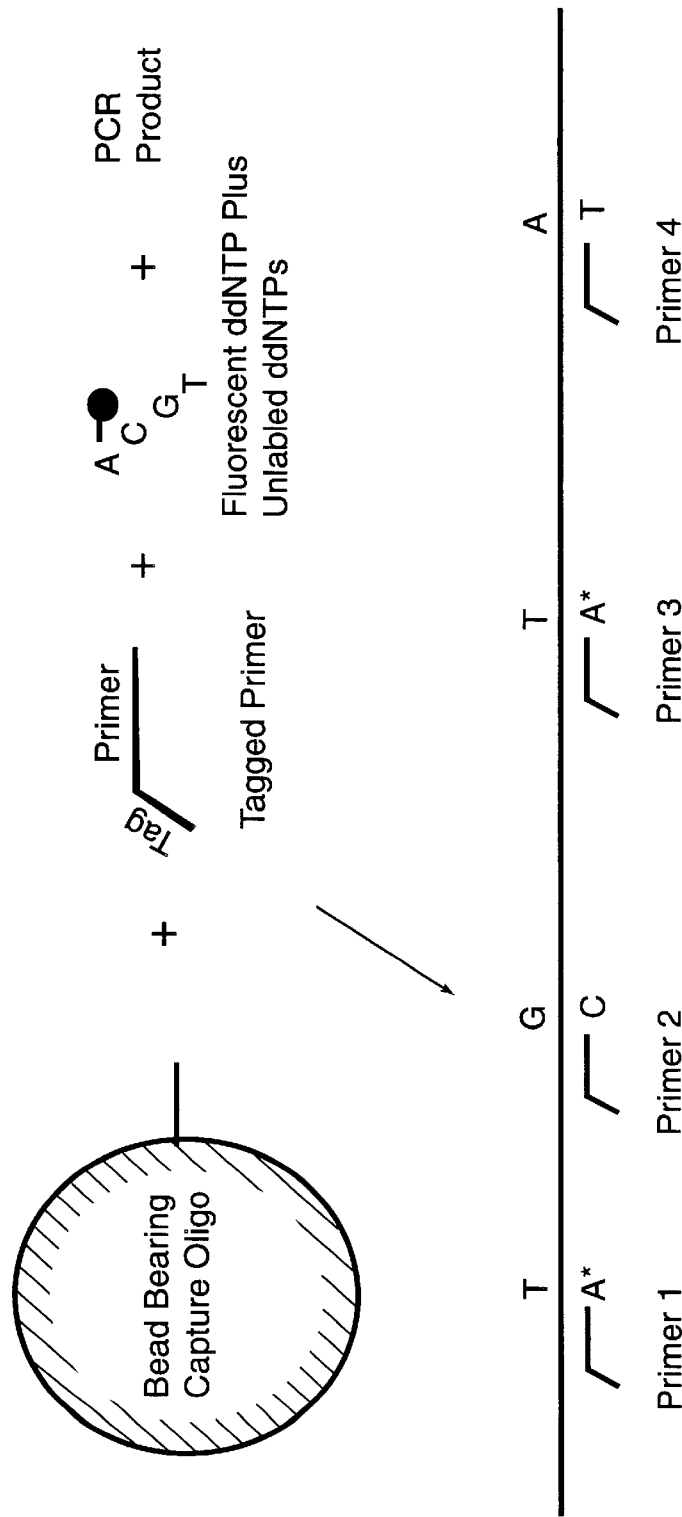

Briefly, the present invention includes the use of oligonucleotide primers, fluorescent dideoxynucleotides, DNA polymerase, microspheres, and flow cytometry to determine DNA base composition at specific sites in a DNA strand. Tagged oligonucleotide primers are incubated with a DNA sample and allowed to anneal immediately adjacent to the site of interest. Fluorescent dideoxynucleotides and DNA polymerase are added and allowed to extend the primer by one base unit, such that upon enzymatic incorporation of the single fluorescent dideoxynucleotide into the DNA strand, the DNA strand can be detected by a flow cytometer. DNA polymerase may be Sequenase, Thermosequenase, or any other conventional or thermostable DNA polymerase.

Another embodiment of the invention uses oligonucleotide primers, oligonucleotide reporters and DNA ligase along with microspheres and flow cytometry to make this determination. A fluorescent reporter oligonucleotide and DNA ligase are added and allowed to ligate the primer to the reporter. The fluorescent reporter oligonucleotides are designed to bind the sample DNA immediately 3' to the annealed oligonucleotide primer. That is, the sequence reporter oligonucleotide is complementary to that of the sample DNA strand except at its 5' terminus, where the reporter is variable so as to interrogate the site of interest on the sample DNA, which can then be investigated by its fluorescent signature using flow cytometry. The DNA, ligase may be any conventional or thermostable ligase. Primer extension or ligation may be enhanced through the use of thermal cycling using heat-stable DNA polymerase or ligase.

Oligonucleotide primers are bound to microspheres either before or after enzymatic extension or ligation. Amino-labeled primers can be covalently attached to carboxylated microspheres using EDAC. Biotinylated primers can be attached to avidin or streptavidin-coated microspheres. Primers bearing an oligonucleotide sequence tag may be annealed to complementary oligonucleotide capture sequences immobilized on microspheres covalently or by the biotin-avidin interaction. Microspheres may be composed of polystyrene, cellulose, or other appropriate material. Microspheres having different sizes, or stained with different amounts of fluorescent dyes, may be used to perform multiplexed sequence analysis.

Having generally described the invention, the following EXAMPLES are intended to provide more specific details thereof.

EXAMPLE 1

Flow Cytometric Minisequencing Using Immobilized Primers:

Reference will now be made in detail to the preferred embodiments of the present invention as illustrated in the accompanying drawings. Turning now to the Figures, FIG. 1a is a schematic representation of microsphere-based minisequencing for flow cytometry, where a primer immobilized on a microsphere is used for hybridizing with the DNA sequence under investigation in the presence of dideoxynucleotides, at least one of which is fluorescently labeled, and polymerase. The primer is extended by one base by the action of the polymerase. FIG. 1b is a schematic representation ol the resulting primer having a single, fluorescent dideoxynucleotide bound to the end thereof which can be detected using flow cytometry, and represents the complementary base to the SNP on the DNA. The sample DNA template is first amplified using the polymerase chain reaction (PCR), and the resulting product treated with shrimp alkaline phosphatase (SAP) and exonuclease I (Exo I) to remove unconsumed deoxynucleotide triphosphates and PCR primers, respectively. The minisequencing primer, designed to interrogate a specific site on the DNA strand under investigation, is immobilized by means of a 5'-amino group on a carboxylated polystyrene microsphere using a cross-linking reagent (e.g., carbodiimide). The primer-bearing microspheres (5 $\mu$l) are added to the amplified DNA (1 $\mu$l, 1 nM) DNA polymerase (one unit, Thermosequenase, Amersham Life Sciences, Cleveland, Ohio), one fluorescein-labeled ddNTP (5 $\mu$M), 5 $\mu$M each of the other three non-fluorescent ddNTPs, and buffer (Thermosequenase buffer, Amersham) in a total volume of 10 $\mu$l. This process was repeated three times using each of the four fluorescent ddNTPs. The reaction mixtures are cycled 99 times at 94° C. for 10 s and at 60° C. for 10 s in a thermal cycler. Two microliters of each reaction mixture were diluted into 500 $\mu$l of TEB buffer (50 mM Tris-HCl, pH, 8.0, 0.5 mM EDTA, 0.5% (w/v) bovine serum albumin, BSA), and the microsphere-associated fluorescence was measured using flow cytometry. Using this procedure, the correct nucleotide base identity was determined for a specific position on an oligonucleotide template with a signal-to-background ratio of greater than one hundred.

EXAMPLE 2

Flow Cytometric Minisequencing Using Biotinylated Primers:

FIG. 2a is a schematic representation of microsphere-based minisequencing for flow cytometry similar to that described in FIGS. 1a and 1b hereof, except that soluble biotinylated primers and avidin-coated capture microspheres are used instead of primers which have already been immobilized on the microspheres. FIG. 2b shows the hybridization of the biotinylated primer to the DNA strand to be investigated and the extension of this primer by a single, fluorescent A dideoxynucleotide (assuming that the SNP is a T base) as a result of the DNA polymerase present in the solution. FIG. 2c shows the capture of the extended biotinylated primer onto an avidin-coated microsphere after the hybridized DNA strand is melted, with the subsequent fluorescence analysis using flow cytometry. The sample DNA template is amplified by PCR, and the resulting product treated with shrimp alkaline phosphatase (SAP) and exonuclease I (Exo I) to remove unconsumed deoxynucleotide triphosphates and PCR primers, respectively. The minisequencing primer, designed to interrogate a specific site on the template DNA, and bearing a 5'-biotin group, is prepared. The biotinylated primer is added to the template DNA (1 $\mu$l, 1 nM), DNA polymerase (one unit, Thermosequenase, Amersham), one fluorescein-labeled ddNTP (5 $\mu$M), 5 $\mu$M each of the other three non-fluorescent ddNTPs, and buffer (Thernosequenase buffer, Amersham) in a total volume of 10 $\mu$l. This process is repeated three times using a different fluorescent ddNTP. The reaction mixtures are cycled 99 times at 94° C. for 10 s and 60° C. for 10 s in a thermal cycler. Five $\mu$l of avidin-coated microspheres are added to the reaction mixture to capture the biotinylated primers. Two microliters of each reaction mixture is diluted into 500 $\mu$l of TEB buffer (50 mM Tris-HCl, pH, 8.0, 0.5 mM EDTA, 0.5% (w/v) bovine serum albumin, BSA), and the microsphere-associated fluorescence is measured using flow cytometry. Using this procedure, the correct nucleotide base identity was determined in thirty out of thirty PCR amplified samples as was confirmed by conventional DNA sequencing techniques.

EXAMPLE 3

Flow Cytometric Minisequencing Using Tagged Primers:

FIG. 3a is a schematic representation of a multiplexed microsphere-based minisequencing procedure using soluble sequence-tagged primers and capture probe-bearing microspheres in a similar manner to the minisequencing illustrated in FIGS. 2a and 2b hereof, except that four SNPs have been assumed to be present on the DNA strand. FIG. 3b illustrates the microspheres and the captured extended primers to be analyzed using flow cytometry. The sample DNA template is amplified by PCR, and the resulting product treated with shrimp alkaline phosphatase (SAP) and exonuclease I (Exo I) to remove unconsumed deoxynucleotide triphosphates and PCR primers, respectively. The minisequencing primer, designed to interrogate a specific site on the template DNA, and bearing a 5'-sequence tag is prepared. A capture probe is designed to bind to the 5'-sequence tag of the primer, and is immobilized on microspheres. The capture tag-bearing primer is added to the template DNA (1 $\mu$l, 1 nM), DNA polymerase (one unit, Thermosequenase, Amersham), one fluorescein-labeled ddNTP (5 $\mu$M), 5 $\mu$M of each of the other three non-fluorescent ddNTPs, and buffer (Thermosequenase buffer, Amersham) in a total volume of 10 $\mu$l. This process is repeated three times using a different fluorescent ddNTP. The reaction mixtures are cycled 99 times at 94° C. for 10 s and 60° C. for 10 s in a thermal cycler. Five microliters of avidin-coated microspheres are added to the reaction mixture to capture the biotinylated primers. Two microliters of each reaction mixture is diluted into 500 $\mu$l of TEB buffer (50 mM Tris-HCl, pH, 8.0, 0.5 mM EDTA, 0.5% (w/v) bovine serum albumin, BSA), and the microsphere-associated fluorescence is measured using flow cytometry.

EXAMPLE 4

Figures 4A, 4B:
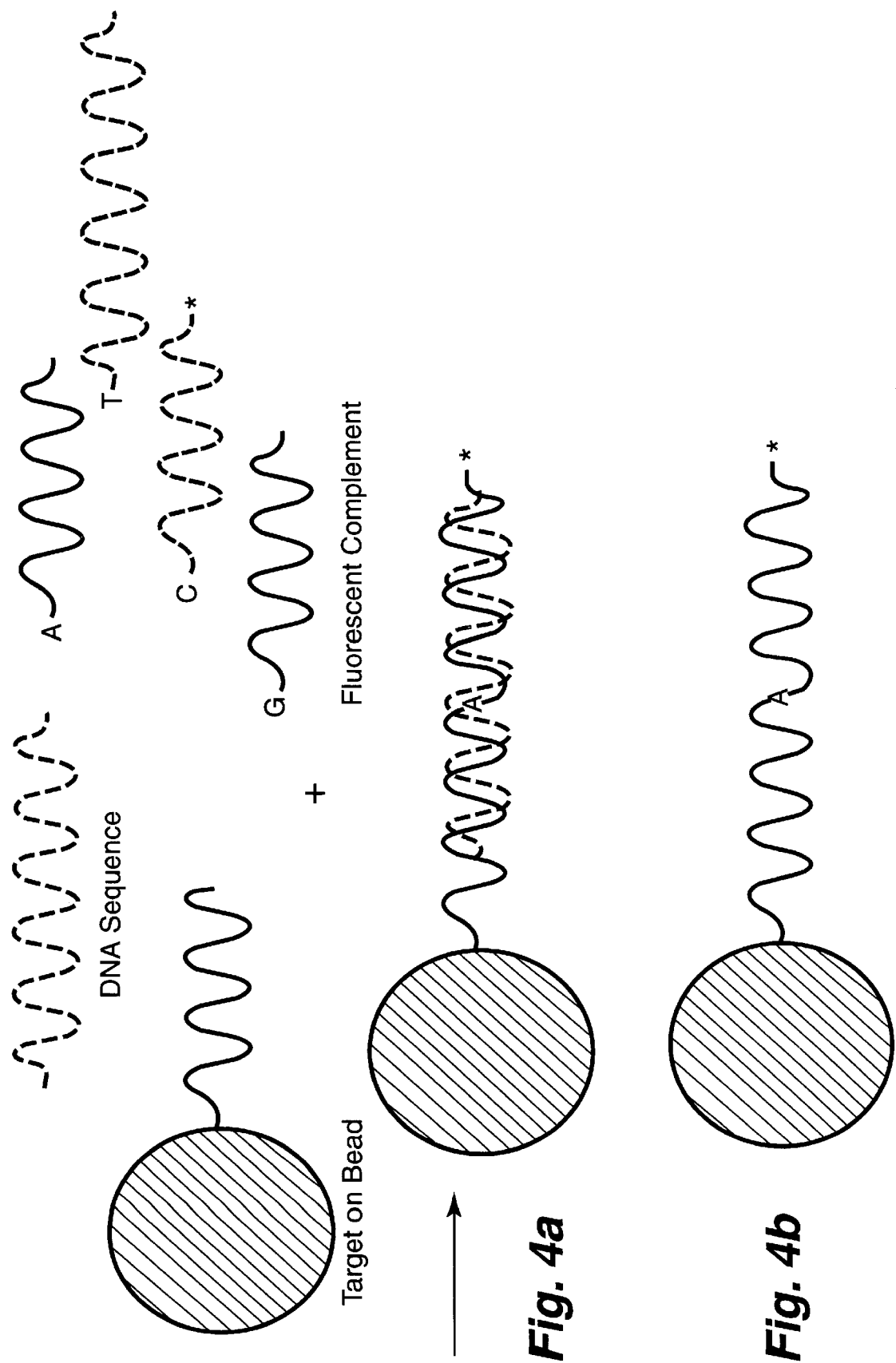

Flow Cytometric Oligonucleotide Ligation Using Immobilized Primers:

FIG. 4a is a schematic representation of microsphere-based oligonucleotide ligation assay using flow cytometry, where a primer immobilized on a microsphere along with fluorescent complementary primers for ligating to the primer which has hybridized to the DNA strand to be investigated in the region of the SNP. FIG. 4b is a schematic representation of the microsphere-attached primer to which the proper fluorescent complement has been ligated after the DNA has been melted away, the flow cytometric determined fluorescence of the microsphere indicating which fluorescent complement has been attached to the DNA strand. The sample DNA template is amplified by PCR, and the resulting product treated with shrimp alkaline phosphatase (SAP) and exonuclease I (Exo I) to remove unconsumed deoxynucleotide triphosphates and PCR primers, respectively. The oligonucleotide ligation primer, designed to interrogate a specific site on the template DNA, is immobilized via a 5'-amino group on a carboxylated polystyrene microsphere using carbodiimide. Four fluorescent reporter oligonucleotides designed to bind immediately adjacent to the site of interest, but varying at the 5'-terminus are prepared. The primer-bearing microspheres (5 $\mu$l) are added to the template DNA (1 $\mu$l, 1 nM), DNA ligase (one unit, Thermoligase, Epicentre Technologies, Madison, Wis.), one fluorescein-labeled reporter oligonucleotide (5 $\mu$M), and buffer (Thermoligase buffer, Epicentre) in a total volume of 10 $\mu$l. This process is repeated three times using each of the four fluorescent reporter oligonucleotides (5 $\mu$M). The reaction mixtures are cycled 99 times at 94° C. for 10 s and 60° C. for 10 s in a thermal cycler. Two microliters of each reaction mixture are diluted into 500 $\mu$l of TEB buffer (50 mM Tris-HCl, pH, 8.0, 0.5 mM EDTA, 0.5% (w/v) bovine serum albumin, BSA), and the microsphere-associated fluorescence is measured using flow cytometry. Using this procedure, the correct nucleotide base identity was determined in thirty out of thirty PCR amplified samples as was confirmed by conventional DNA sequencing techniques.

EXAMPLE 5

Figures 5A, 5B:
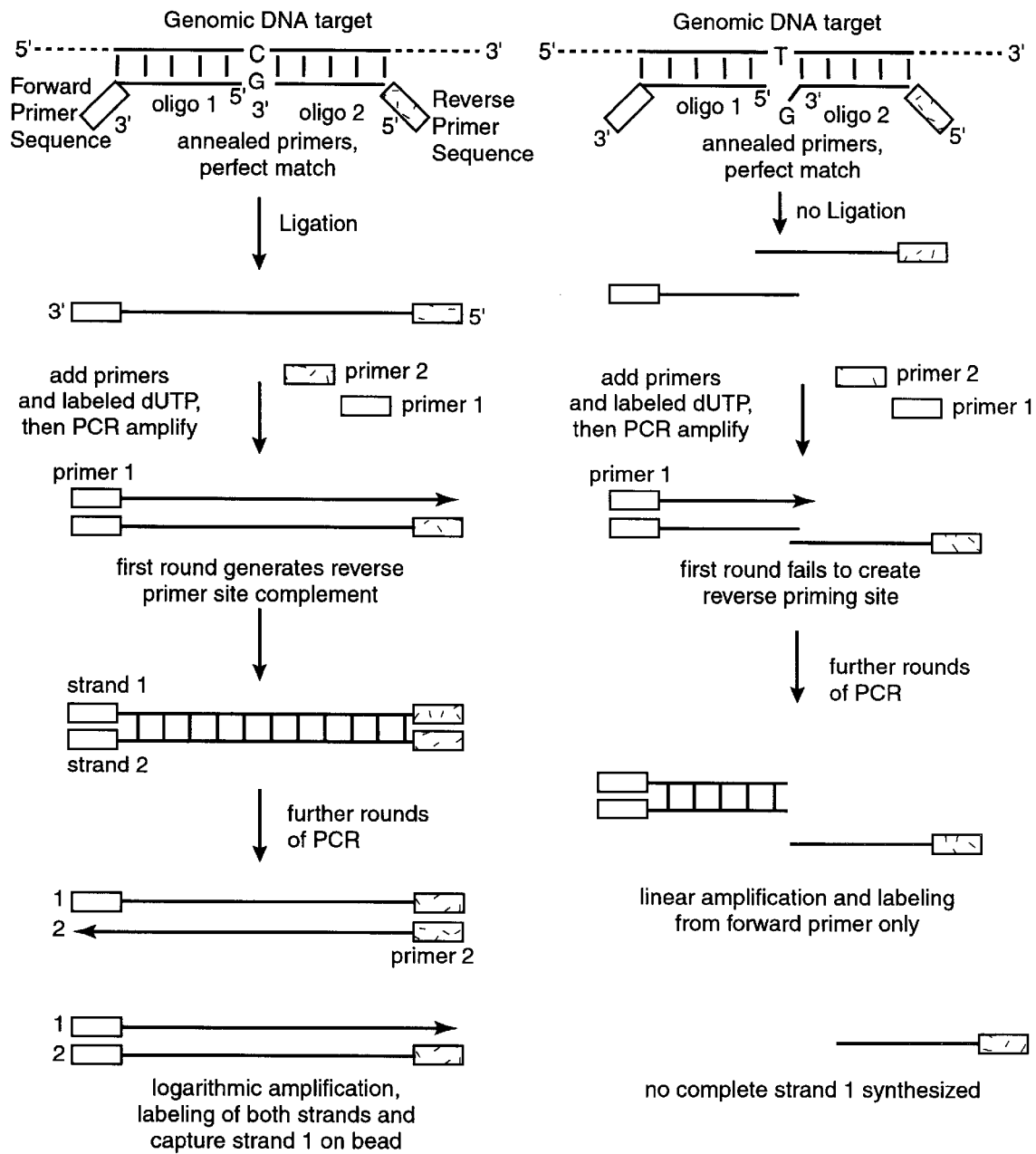
FIGS. 5a and 5b are schematic representations of oligonucleotide ligation on unamplified DNA, followed by PCR amplification, capture on microspheres, and analysis of microsphere fluorescence by flow cytometry, for the case where the complementary base is found on the DNA strand and where the complementary base does not exist on the DNA strand, respectively.

Multiplexed Oligonucleotide Ligation on Unamplified DNA, Followed by PCR Amplification:

FIGS. 5a and 5b are schematic representations of oligonucleotide ligation on unamplified DNA, followed by PCR amplification, capture on microspheres, and analysis of microsphere fluorescence by flow cytometry, for the case where the complementary base is found on the DNA strand and where the complementary base does not exist on the DNA strand, respectively.

A set of oligonucleotide primers is designed including one oligonucleotide (oligonucleotide 1) that is complementary to the sequence of the template DNA immediately adjacent to a site of interest, and four oligonucleotides (oligonucleotides 1A, 1C, 1G, and 1T) that are complementary to the sequence of the template DNA immediately adjacent to oligonucleotide 1, and containing the site of interest. Each of the four oligonucleotides (1A, 1C, 1G, and 1T) differs in the nucleotide base adjacent to the other oligonucleotide (oligonucleotide 1), corresponding to each of the four possible bases, A, C, G, and T. Oligonucleotide 1 is intended to ligate to one of the other oligonucleotides (1A, 1C, 1G, or 1T), depending which one contains the complementary base for the site of interest. In addition, each of the two oligonucleotides in a potential pair (five oligonucleotides total) contain additional nucleotides that form a "tail" consisting of a PCR priming site. This site is different for oligonucleotide 1 than for oligonucleotides 1A, 1C, 1G, and 1T, which have the same primer-binding site within this group, but different from that of oligonucleotide 1. Four parallel ligation reactions are performed, each with oligonucleotide 1, one each of the other oligonucleotides (1A, 1C, 1G, or 1T) and a DNA ligase enzyme. All oligonucleotides are expected to hybridize to the template, but only the oligonucleotide with a perfect match will be ligated to oligonucleotide 1. The resulting ligation product will serve as the template for a PCR reaction that follows using one primer (primer 1) complementary to the tail introduced into oligonucleotide 1, and the other primer (primer 2) having the same sequence as that of the tail of oligonucleotides 1A, 1C, 1G, and 1T. Unligated, oligonucleotides cannot be amplified with the PCR technique (FIG. 5b) because there is no priming site for oligonucleotide 2 unless PCR amplification from primer 1 extends across a ligated fragment, creating sequence complementary to primer 2. In addition to unlabeled dNTPs used during the PCR step, fluorescently labeled dNTPs are added to label the PCR fragments during amplification. Alternatively, primer 2 is labeled with a fluorescent dye, producing dye-labeled PCR amplification products where amplification occurs.

The final step involves adding to the PCR mixture microspheres with an oligonucleotide immobilized on its surface that has the same sequence as oligonucleotides 1A, 1C, 1G, and 1T, except for the variable nucleotide at one end and the priming site on the other. This microsphere is intended to capture labeled PCR products if they are present in the PCR mixture by annealing to the newly synthesized complement of the ligated oligonucleotide complex. Bead fluorescence due to hybridized fragments is then analyzed by flow cytometry. Many sets of primers can simultaneously type many SNPs in solution, each being captured onto a different bead in a multiplexed set to be simultaneously read in a flow cytometer.

The foregoing description of the invention has been presented for purposes of illustration and description and is not intended to be exhaustive or to limit the invention to the precise form disclosed, and obviously many modifications and variations are possible in light of the above teaching. For example, in order to bind the oligonucleotide primers to the microspheres for analysis using flow cytometry, the oligonucleotide primers may include a sequence tag which is hybridized to a capture probe that is complementary to the sequence tag and is immobilized on the microspheres, the sequence tags and capture probes containing at least one of the nonnatural bases iso-C and 5-methyl-iso-G. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims, appended hereto.

What is claimed is:

1. A homogeneous method for determining the identity of a base on a DNA strand, which comprises in order the steps of:
    (a) immobilizing an oligonucleotide which is capable of being annealed to the DNA strand immediately adjacent to the base whose identity is to be determined on a microsphere;
    (b) annealing the oligonucleotide to the DNA strand;
    (c) incubating the microspheres to which the DNA strand has annealed to the immobilized oligonucleotide with four different dideoxynucleotides, one of the dideoxynucleotides having a reporter molecule in the presence of an enzyme, thereby extending the immobilized oligonucleotide by one base unit; and
    (d) analyzing the microsphere using flow cytometry whereby the identity of the base is determined.

2. The method as described in claim 1, wherein the reporter is fluorescent and the enzyme is a DNA polymerase.

3. The method as described in claim 1, wherein the oligonucleotide is biotinylated and the microsphere is coated with avidin or streptavidin.

4. The method as described in claim 1, wherein the microsphere is biotinylated and the oligonucleotide is coupled to avidin or streptavidin.

5. The method as described in claim 1, wherein the oligonucleotide is covalently attached to the microsphere.

6. The method as described in claim 1, wherein the oligonucleotide is hybridized to a complementary capture probe immobilized on a microsphere.

7. The method as described in claim 6, wherein the oligonucleotide comprises a sequence tag which is hybridized to the capture probe, and wherein the sequence tag and capture probe comprises a non-natural base selected from the group consisting of iso-C and 5-methyl-iso-G.

8. A homogeneous method for determining the identity of a base on a DNA strand, which comprises in order the steps of:
    (a) annealing an oligonucleotide to the DNA strand immediately adjacent to the base whose identity is to be determined;
    (b) incubating the annealed DNA strand and oligonucleotide with four different dideoxynucleotides, one of the dideoxynucleotides having a reporter molecule in the presence of an enzyme, thereby extending the oligonucleotide by one base unit;
    (c) immobilizing the extended oligonucleotide on a microsphere; and
    (d) analyzing the microsphere using flow cytometry whereby the base under investigation is determined.

9. The method of claim 8, wherein the reporter molecule is fluorescent and said fluorescent reporter molecule contains a fluorescent dideoxynucleotide and the enzyme is a DNA polymerase.

10. The method as described in claim 8, wherein the oligonucleotide is biotinylated and the microsphere is coated with avidin or streptavidin.

11. The method as described in claim 8, wherein the microsphere is biotinylated and the oligonucleotide is coupled to avidin or streptavidin.

12. The method as described in claim 8, wherein the oligonucleotide as covalently attached to the microsphere.

13. The method as described in claim 8, wherein the oligonucleotide is hybridized to a complementary capture probe immobilized on a microsphere.

14. The method as described in claim 13, wherein the oligonucleotide comprises a sequence tag which is hybridized to the capture probe, and wherein the sequence tag and capture probe comprises at least one non-natural base selected from the group consisting of iso-,C and 5-methyl-iso-G.

15. A homogeneous method for determining the identity of a base at a site on a DNA strand, which comprises in order the steps of
(a) annealing a first oligonucleotide to the DNA strand immediately adjacent to the base and a second oligonucleotide to the DNA strand adjacent to the first oligonucleotide and in the presence of an enzyme, wherein the second oligonucleotide contains both a reporter molecule and an interrogator base that is complementary to the base whose identity is being determined and wherein the second oligonucleotide attaches to the first oligonucleotide forming a ligated oligonucleotide;
(b) denaturing the DNA strand and immobilizing the ligated oligonucleotide on a microsphere; and
(c) analyzing the microsphere using flow cytometry whereby the identity of the base is determined.

16. The method as described in claim 15 wherein the reporter molecule is fluorescent, and the enzyme is a DNA polymerase.

17. The method as described in claim 15 wherein the first oligonucleotide is biotinylated and the microsphere is coated with avidin or streptavidin.

18. The method as described in claim 15 wherein the microsphere is biotinylated and the first oligonucleotide is coupled to avidin or streptavidin.

19. The method as described in claim 15 wherein the first oligonucleotide is covalently attached to the microsphere.

20. The method as described in claim 15 wherein the first oligonucleotide is hybridized to a complementary capture probe immobilized on a microsphere.

21. The as described in claim 20, wherein a sequence tag is hybridized to capture probe that is complimentary thereto, and wherein the sequence tag and the capture probe comprises a non-natural base selected from the group consisting of iso-C and 5-methyl-iso-G.

* * * * *